(12) United States Patent
Arab (10) Patent No.: US 8,717,568 B2
(45) Date of Patent: May 6, 2014

(54) ANALYZING PARTICLE QUANTITY AND/OR DISTRIBUTION WITHIN AN ASSAY ANALYSIS SYSTEM

(75) Inventor: Nicolas Arab, Austin, TX (US)

(73) Assignee: Luminex Corporation, Austin, TX (US)

( * ) Notice: Subject to any disclaimer, the term of this patent is extended or adjusted under 35 U.S.C. 154(b) by 402 days.

(21) Appl. No.: 13/184,100

(22) Filed: Jul. 15, 2011

(65) Prior Publication Data

US 2012/0019536 A1  Jan. 26, 2012

Related U.S. Application Data (60) Provisional application No. 61/364,879, filed on Jul. 16, 2010.

(51) Int. Cl.
*G01N 21/25* (2006.01)
*G01B 11/06* (2006.01)
*G06K 9/00* (2006.01)

(52) U.S. Cl.
USPC ............ 356/436; 356/441; 356/432; 356/38; 382/280; 382/191; 382/207; 382/210

(58) Field of Classification Search
USPC ............ 356/38, 39, 432–442; 382/280, 191, 382/207, 210
See application file for complete search history.

(56) References Cited

U.S. PATENT DOCUMENTS

| | | | |
|---|---|---|---|
| 5,072,382 A | 12/1991 | Kamentsky | 382/133 |
| 5,114,350 A * | 5/1992 | Hewett | 435/286.4 |
| 5,235,428 A | 8/1993 | Hirota et al. | 348/355 |
| 5,962,238 A | 10/1999 | Sizto et al. | 435/7.24 |
| 7,123,750 B2 | 10/2006 | Lu et al. | 382/110 |
| 2003/0206302 A1 * | 11/2003 | Pugh | 356/436 |
| 2007/0064990 A1 | 3/2007 | Roth | 382/128 |
| 2007/0281311 A1 | 12/2007 | Roth et al. | 435/6.11 |
| 2009/0071225 A1 | 3/2009 | Schilffarth | 73/1.02 |
| 2010/0017358 A1 | 1/2010 | Roth | 706/54 |

FOREIGN PATENT DOCUMENTS

WO  WO 2008/098284  8/2008

OTHER PUBLICATIONS

International Search Report and Written Opinion, issued in International Patent Application No. PCT/US2011/044152, mailed on Mar. 15, 2012.

Momota, et al., "Measuring particle size distribution by digital image processing with inverse fourier-bessel transformation," *Jpn. J. Appl. Phys.*, 33:1189-94, 1994.

\* cited by examiner

*Primary Examiner* — Gregory J Toatley
*Assistant Examiner* — Rebecca C Bryant
(74) *Attorney, Agent, or Firm* — Meyertons, Hood, Kivlin, Kowert & Goetzel, P.C.

(57) ABSTRACT

Methods, storage mediums and systems (MS&S) are provided which successively image an imaging region of an assay analysis system (AAS) as particles are loaded into the imaging region, generate a frequency spectrum of each image via a discrete Fourier transform, integrate a same coordinate portion of each frequency spectrum and terminate the loading of particles upon computing an integral which meets preset criterion. In addition, MS&S are provided which send a signal indicative of whether enough particles are in an imaging region for further processes by an AAS based on the magnitude of integral calculated from an image's frequency spectrum. MM&S are also provided such that the steps of generating a frequency spectrum of each image and integrating a portion of each frequency spectrum are replaced by generating a convolved spatial image with a filter kernel and integrating a same coordinate portion of each convolved spatial image.

20 Claims, 5 Drawing Sheets

ANALYZING PARTICLE QUANTITY AND/OR DISTRIBUTION WITHIN AN ASSAY ANALYSIS SYSTEM

The present application claims the benefit of U.S. Provisional Application No. 61/364,879 filed Jul. 16, 2010. The entire contents of which is specifically incorporated herein by reference without disclaimer.

BACKGROUND OF THE INVENTION

1. Field of the Invention

This invention generally relates to methods, storage mediums, and systems for analyzing particle quantity and distribution within an imaging region of an assay analysis system and, further, to methods, storage mediums, and systems for evaluating the performance of a focusing routine performed on an assay analysis system.

2. Description of the Related Art

The following descriptions and examples are not admitted to be prior art by virtue of their inclusion within this section.

Fluid assays are used for a variety of purposes, including but not limited to biological screenings and environmental assessments. Often, particles are used in fluid assays to aid in the detection and quantification of one or more analytes of interest within a sample. In particular, particles provide substrates for carrying reagents configured to react with analytes of interest within a sample such that the analytes may be detected. In some cases, a multiplexing scheme is employed in assay analysis systems such that multiple analytes may be evaluated in a single analysis process for a single sample. To facilitate a multiplexing scheme, particles are configured into distinguishable groups and each group is used to indicate the presence, absence, and/or amount of a different analyte in an assay. The different particle subsets may be distinguishable, for example, by different fluorescent dyes and/or different concentrations of dyes absorbed into particles and/or bound to the surface of particles. In addition or alternatively, the size of particles among the different subsets may vary. In any case, optical imaging instruments may be used to analyze fluid assays induced with particles. More specifically, optical imaging instruments may be configured to image particles within an illuminated region of a chamber in which an assay is introduced and may be further configured to analyze the imaged particles for the detection and quantification of one or more analytes of interest.

It is often advantageous to monitor the quantity of particles introduced into the chamber to insure an appropriate amount is in the imaging region for analysis of the sample. In particular, if an imaging region is overpopulated with particles, at least some of the particles will crowd each other causing them to reflect each other's light and falsely convey a brighter intensity. On the contrary, if the number of particles within an imaging region is not enough to constitute statistically significant data regarding the detection and quantification of analytes of interest within a sample (which may be particularly applicable in multiplexing schemes), then the processes of imaging the particles and processing the data acquired therefrom are performed in vain. In some cases, the number of particles within the imaging region (particularly when there is not enough particles within the imaging region) may affect the accuracy of an autofocus routine performed on the imaging system, which in turn will affect the resolution of any image taken and consequently skew data acquired therefrom.

In many instances, the number of particles delivered into the imaging chamber is estimated based on expected particle densities present in the sample volume. Particle densities, however, can vary substantially from sample to sample and, thus, such a technique requires the particle density of a sample to be known and inputted into a system prior to injecting the sample into the imaging chamber. Some assay analysis techniques involve counting particles within an imaging chamber. For example, spatial-domain image analysis is often performed using thresholding for edge or peak detection of particles. Thresholding, however, can become complicated if particle brightness varies significantly (such as in a multiplexing scheme). Furthermore, once an edge or peak has been detected, a neighborhood of pixels must be assembled that identifies an imaged particle, which can sometimes be time-consuming. Thus, spatial-domain image analysis is not generally considered advantageous for monitoring the quantity of particles introduced into a chamber.

In an optical imaging instrument that must accurately measure the amount of fluorescent light emitted from each observed particle, particle distribution within an imaging region is as important as quantity. In particular, similar to the overpopulation of particles within an imaging region, particles that are clustered together may induce measurable reflections and falsely convey a brighter intensity. Moreover, light collected from a cluster of particles is generally difficult to differentiate on a particle-by-particle basis. To overcome this problem, particle clusters will often be ignored during analysis. Therefore, two imaging volumes containing an equal population of particles but different distributions will yield different amounts of useful data. In order to identify the particle clusters, spatial-domain image analysis as described above for particle counting is often performed. Such a technique, however, is generally not used to determine particle distribution in an imaging volume nor would it be considered a viable option, particularly as particles are being introduced into an imaging chamber, due to its time constraints.

In addition to the number of particles arranged within an imaging region of an optical assay analysis system, the configuration of the system affects the accuracy of the data obtained from an image. In particular, it is important that the focal position of the photosensitive detection subsystem is optimized such that image resolution is optimized and accurate data is obtained. In light of its importance, many optical analysis systems employ an automated routine for periodically optimizing the focal position of its photosensitive detection subsystem. In many cases, however, characteristics and/or operation of an optical analysis system may change over time and, in some embodiments, the changes may affect a routine's ability to optimize a focal position of a photosensitive detection subsystem.

Accordingly, it would be beneficial to develop methods, program instructions, and systems for evaluating the performance of a focusing routine performed on an optical assay analysis system. Furthermore, it would be desirable to develop methods, program instructions, and systems for analyzing particle quantity and distribution within an imaging region of an optical assay analysis system, particularly as particles are delivered into the imaging region. More specifically, it would be advantageous to develop methods, program instructions, and systems for analyzing the quantity of particles within an imaging chamber to insure an appropriate amount is present for further processes conducted by the system.

SUMMARY OF THE INVENTION

The following description of various embodiments of methods, storage mediums, and systems for analyzing particle quantity and distribution within an imaging region of an assay analysis system and various embodiments of methods, storage mediums, and systems for evaluating the performance of a focusing routine performed on an assay analysis system is not to be construed in any way as limiting the subject matter of the appended claims.

Embodiments of the methods, storage mediums, and systems include configurations for successively imaging an imaging region of an assay analysis system as particles are loaded into the imaging region, generating a frequency spectrum of each image via a discrete Fourier transform upon formation of each image, and integrating a same coordinate portion of each frequency spectrum. Alternatively, some embodiments of the methods, storage mediums, and systems, include configurations for successively imaging an imaging region of an assay analysis system as particles are loaded into the imaging region, generating a convolved spatial image of each image by convolving each image with a kernel (e.g., a band pass or a high pass filter). In some cases, the methods, storage mediums, and systems include configurations for terminating the loading of particles into the imaging region upon computing an integral that crosses a predetermined threshold. In other embodiments, the methods, storage mediums, and systems include configurations for tracking integrals calculated for the successively generated frequency spectrums and terminating the loading of particles upon detecting a change in integral magnitude less than a preset limit between two frequency spectrums generated in succession. Similarly, in some embodiments, the methods, storage mediums, and systems include configurations for tracking integrals calculated for the successively generated convolved spatial images and terminating the loading of particles upon detecting a change in integral magnitude less than a preset limit between two convolved spatial images generated in succession.

Other embodiments of the methods, storage mediums, and systems include configurations for generating, via a discrete Fourier transform, a frequency spectrum of an image generated by an assay analysis system and integrating a portion of the frequency spectrum. The methods, storage mediums, and systems further include configurations for sending a first signal indicating enough particles are in the imaging region for further processes by the assay analysis system upon calculating an integral greater than a predetermined threshold. In addition, the methods, storage mediums, and systems include configurations for sending a second signal indicating not enough particles are in the imaging region for further processes by the assay analysis system upon calculating an integral less than the predetermined threshold.

Similarly, other embodiments of the methods, storage mediums, and systems include configurations for generating convolved spatial image generated by an assay analysis system and integrating a portion of the convolved spatial image. The methods, storage mediums, and systems further include configurations for sending a first signal indicating enough particles are in the imaging region for further processes by the assay analysis system upon calculating an integral greater than a predetermined threshold. In addition, the methods, storage mediums, and systems include configurations for sending a second signal indicating not enough particles are in the imaging region for further processes by the assay analysis system upon calculating an integral less than the predetermined threshold.

Yet other embodiments of the methods, storage mediums, and systems include configurations for performing an automated routine to optimize a focal position of a photosensitive detection subsystem of a assay analysis system and imaging particles arranged within an imaging region of the assay analysis system subsequent to performing the automated routine. The methods, storage mediums, and systems further include configurations for generating a frequency spectrum of the image via a discrete Fourier transform and comparing a width of a primary lobe of the frequency spectrum at a designated brightness value to a benchmark to evaluate the performance of the automated routine. The methods, storage mediums, and systems additionally include configurations for generating a convolved spatial image of the image comparing portion of the generated convolved spatial image to a threshold to evaluate the performance of the automated routine.

BRIEF DESCRIPTION OF THE DRAWINGS

Other objects and advantages of the invention will become apparent upon reading the following detailed description and upon reference to the accompanying drawings in which.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Figure 1:
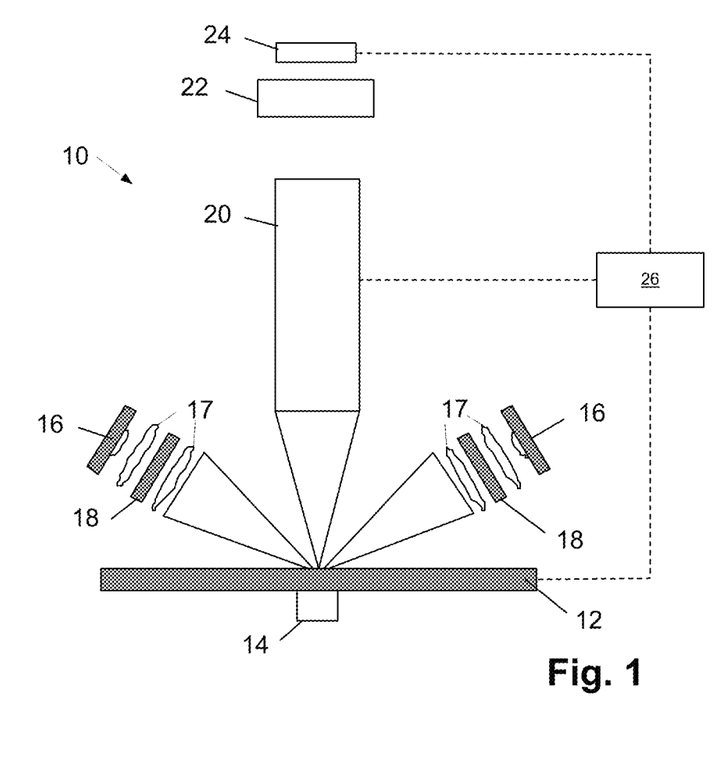
FIG. 1 is a schematic diagram of an optical assay analysis imaging system.
Figure 2:
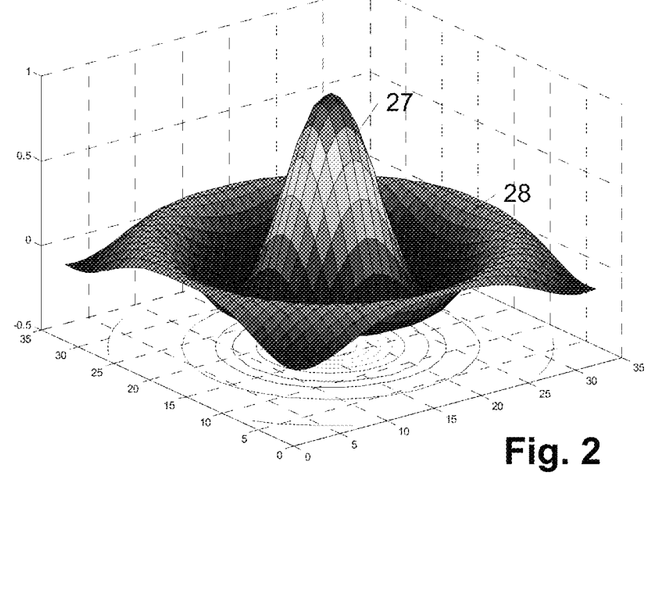
FIG. 2 is an example of a frequency spectrum of an image of particles generated via a discrete Fourier transform.
Figure 3:
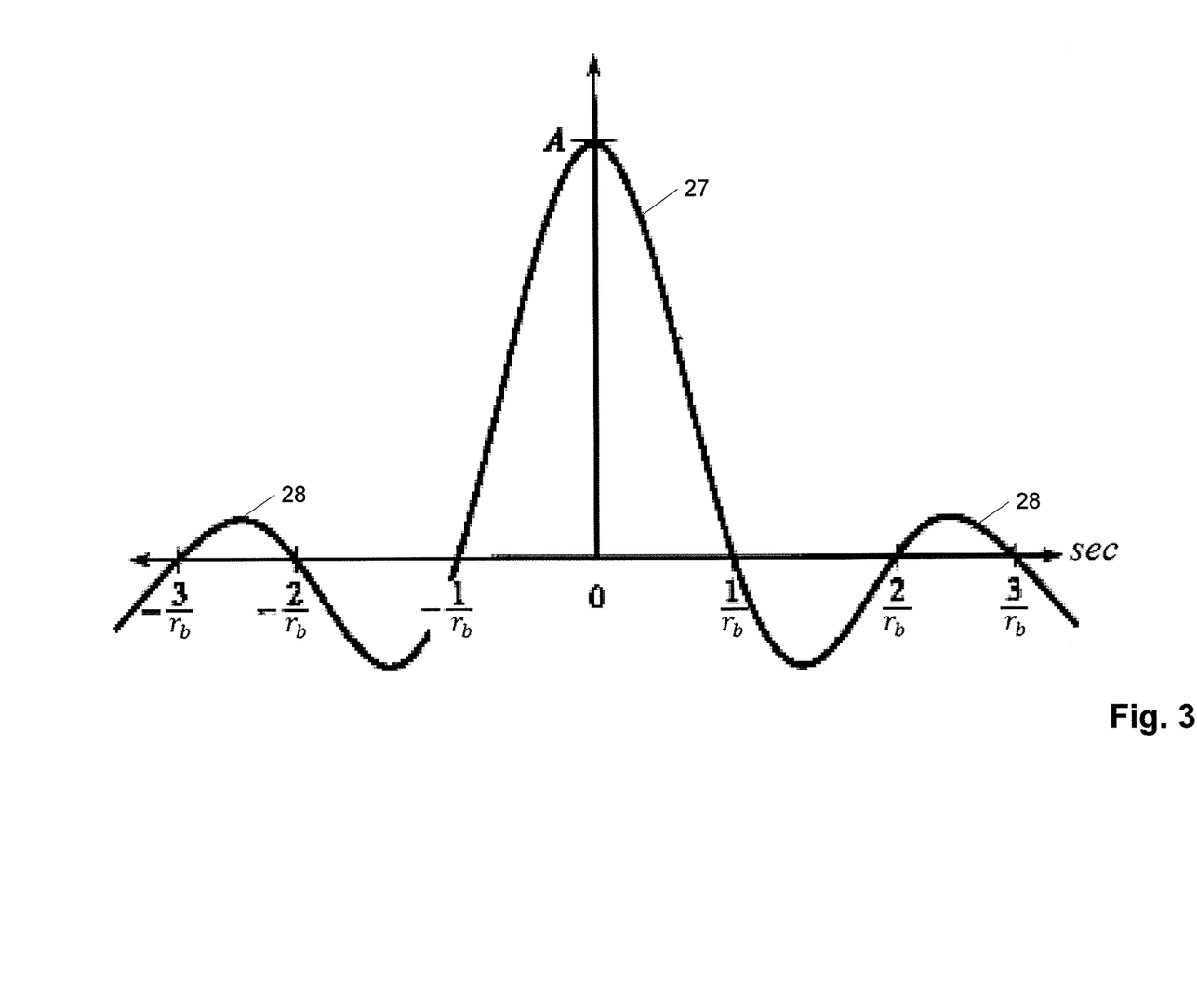
FIG. 3 is a cross-sectional view of the frequency spectrum shown in FIG. 2.
Figure 4A:
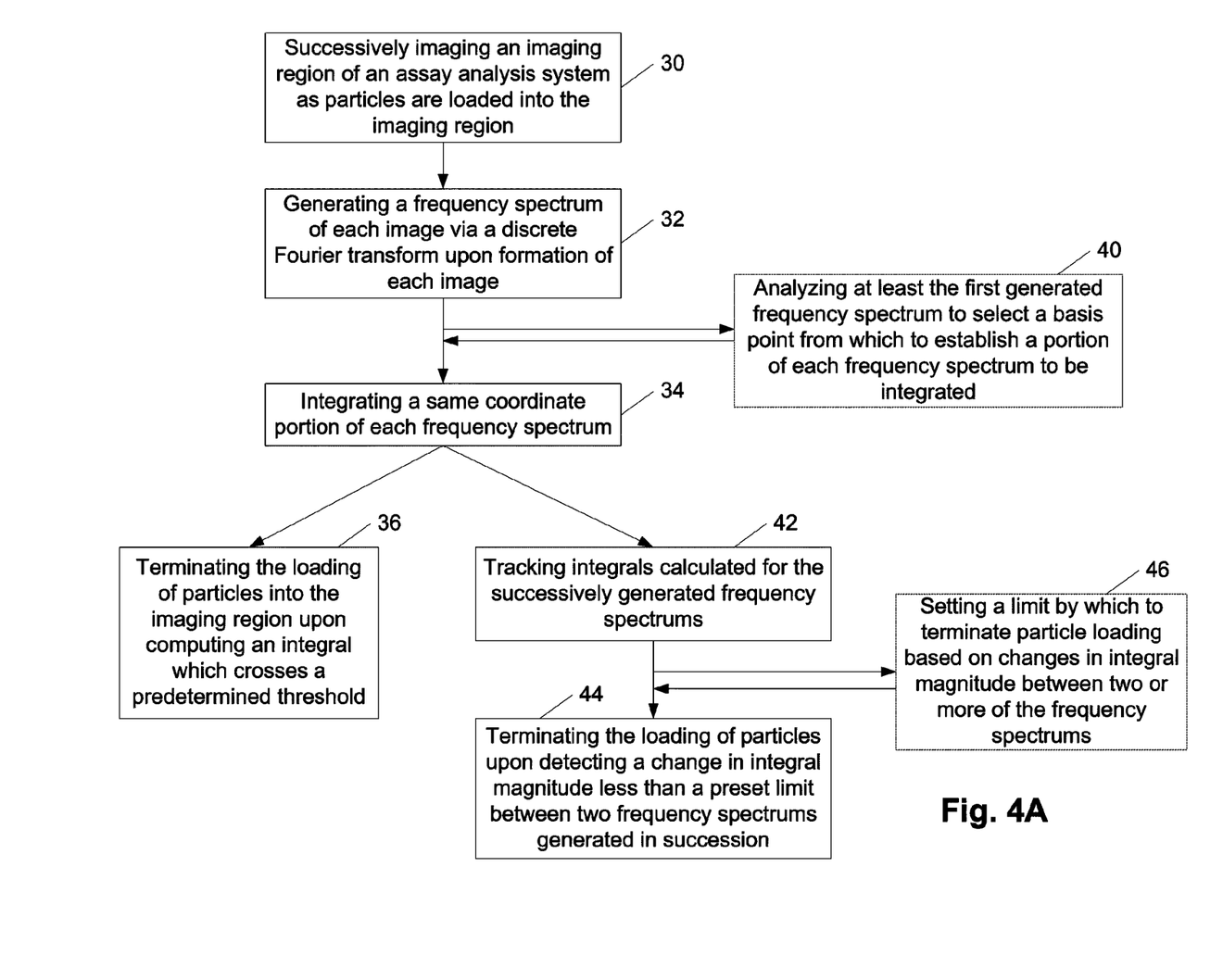
FIGS. 4A and 4B are flowcharts of a method for analyzing particle quantity and distribution within an imaging region of an optical assay analysis system as particles are loaded into the imaging region to determine when to terminate the loading of particles.
Figure 4B:
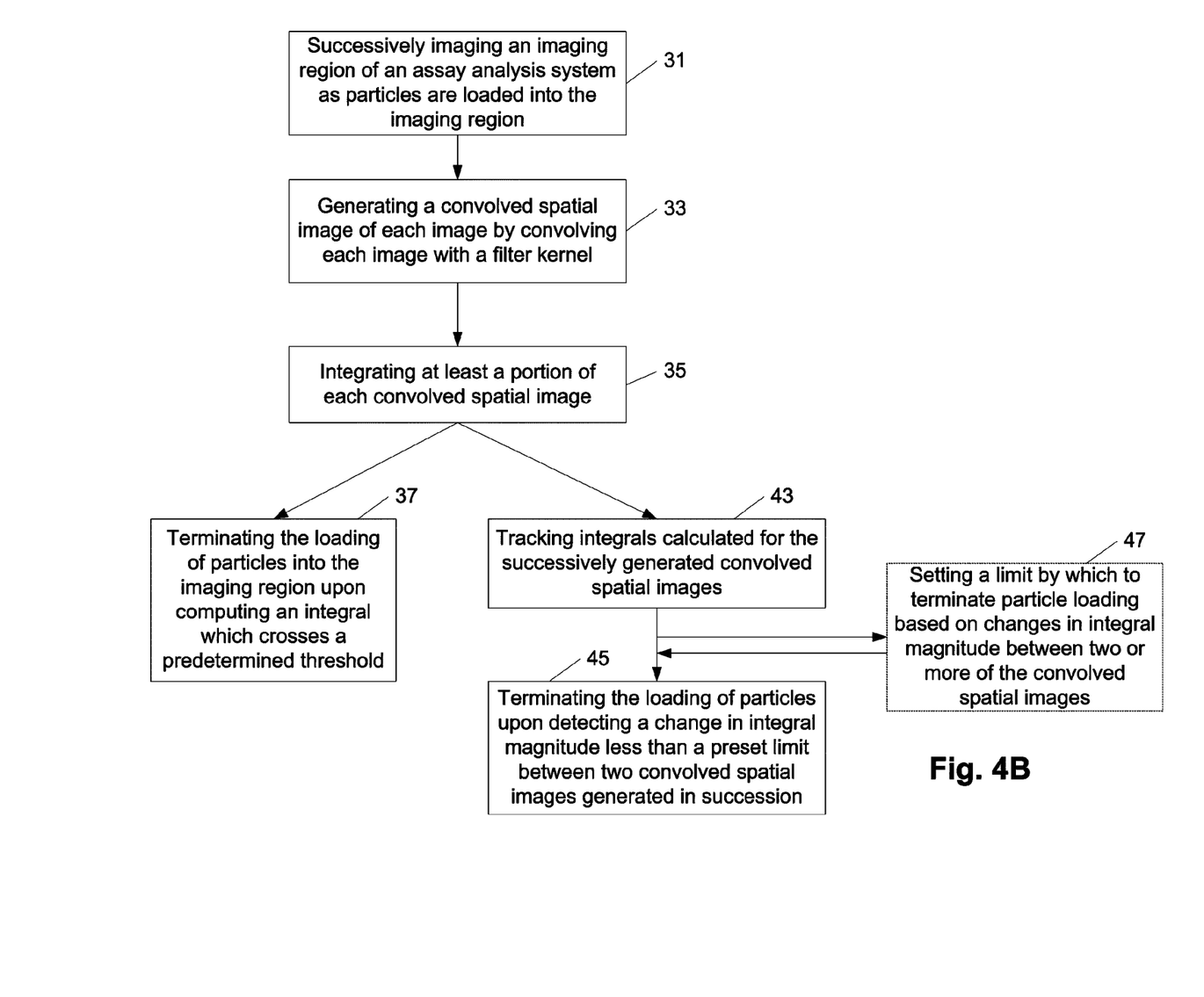
Figure 5:
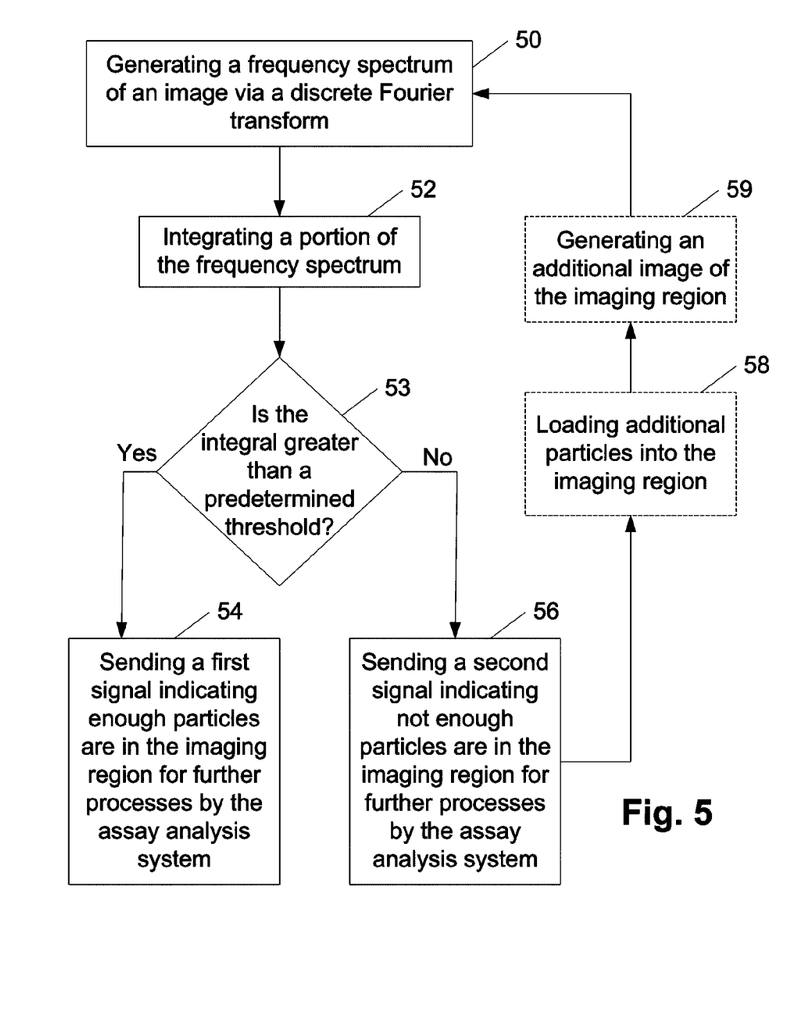
FIG. 5 is a flowchart of a method for analyzing particle quantity within an imaging region of an optical assay analysis system to determine if enough are present for further processes by the assay analysis system.
Figure 6:
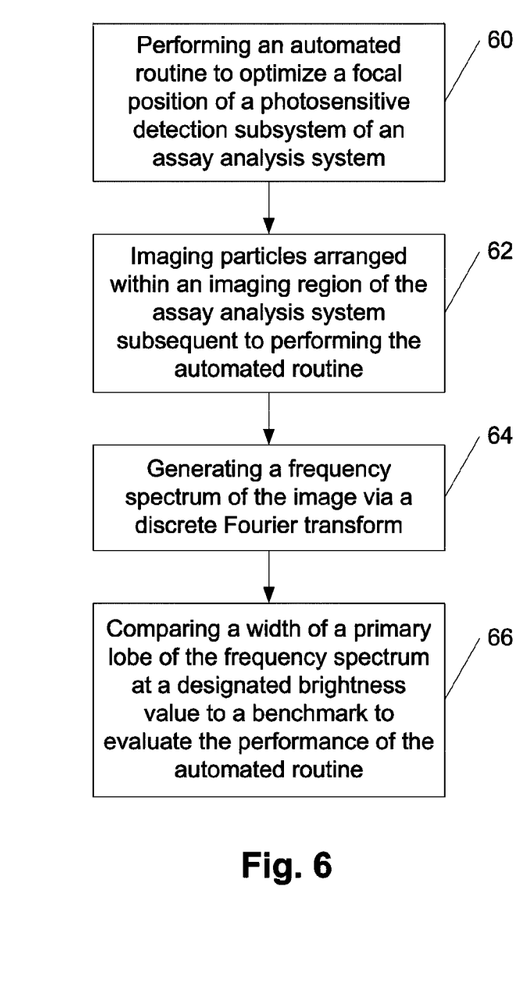
FIG. 6 is a flowchart of a method for evaluating the performance of a focusing routine performed on an optical assay analysis system.

Turning to the drawings, exemplary methods, storage mediums, and systems for analyzing particle quantity and distribution within an imaging region of an assay analysis system are provided. In addition, exemplary methods, storage mediums, and systems for evaluating the performance of a focusing routine performed on an assay analysis system are provided. In particular, FIGS. 4 and 5 depict flowcharts for analyzing particle quantity and distribution within an imaging region of an assay analysis system. FIG. 6, on the other hand, depicts a flowchart for evaluating the performance of a focusing routine performed on an assay analysis system. An exemplary optical assay analysis system is depicted in FIG. 1 having a storage medium which includes program instructions configured to perform the processes outlined in the flowcharts depicted in FIGS. 4-6. FIGS. 2 and 3 illustrate graphical representations of an exemplary frequency spectrum generated via a discrete Fourier transform for an image of particles. As described in more detail below, some embodiments of the methods described herein involve generating a frequency spectrum of an image via a discrete Fourier transform and analyzing the frequency spectrum to obtain information about the state of the assay analysis system used to create the image. Other embodiments of the methods described herein involve generating a convolved spatial image of an image by convolving the image with a filter kernel. It is noted that the methods, storage mediums, and systems described herein are not necessarily limited to the illustrations of FIGS. 1-6. In particular, the systems described herein may include additional or alternative features not shown in FIG. 1 and the frequency spectrums and convolved spatial images generated using the systems described herein may be of many alternative forms, including but not limited to that depicted in FIGS. 2 and 3. In addition, the methods described herein may, in some cases, be configured to perform processes other than those depicted in FIGS. 4-6.

As noted above, FIG. 1 illustrates a schematic of an exemplary optical assay analysis system, particularly the optic and control components of the system. In particular, FIG. 1 illustrates assay analysis system 10 including an illumination subsystem comprising light sources 16, lenses 17 and filters 18 configured to illuminate an imaging region of analysis chamber 12. In addition, assay analysis system 10 includes a photosensitive detection subsystem comprising imaging lens 20, filter/s 22 and photosensitive detector 24 configured to image particles arranged within the imaging region of analysis chamber 12 when illuminated. Furthermore, assay analysis system 10 may include processing unit 26 operatively coupled (as denoted by the dotted lines in FIG. 1) to different components of the system, such as but not limited to components of analysis chamber 12, the illumination subsystem and the photosensitive subsystem. As described in more detail below, processing unit 26 includes a processor and a storage medium having program instructions which are executable via the processor for performing a number of operations on assay analysis system 10. It is noted that the operative coupling of processing unit 26 is not limited to the depiction of dotted lines in FIG. 1. In particular, processing unit 26 may be operatively coupled to any component of assay analysis system 10, including those not shown in FIG. 1 such as components of a fluidic handling system.

In general, analysis chamber 12 is configured to provide an optically clear path to its imaging region such that the region may be illuminated and imaged by the respective illumination and photosensitive detection subsystems of assay analysis system 10 as discussed above. In addition, analysis chamber 12 may include any configuration suitable for transporting a fluid assay having particles into and out of its imaging region. As described below, the photosensitive detection subsystem of assay analysis system 10 is configured to collect light reflected from particles in the imaging region and thus, the photosensitive detection subsystem is arranged on the same side of analysis chamber 12 as the illumination subsystem. In some cases, assay analysis system 10 may include immobilization subsystem 14 disposed on the other side of analysis chamber 12 for immobilizing particles within the imaging region of the chamber. In particular, particle immobilization may ensure particles are in a stationary position and within the same plane for imaging. In other cases, however, immobilization subsystem 14 may be omitted from assay analysis system 10. In such embodiments, analysis chamber 12 may be configured to distribute particles of a fluid assay in a single plane within its imaging region.

As shown in FIG. 1, the illumination subsystem of assay analysis system 10 (i.e., light sources 16, lenses 17 and filters 18) may be configured to illuminate the imaging region of analysis chamber 12 at an acute angle relative to plane of the imaging region. Such an arrangement allows the photosensitive detection subsystem (i.e., imaging lens 20, filter/s 22 and photosensitive detector 24) to be centrally arranged above the imaging region of analysis chamber 12. Other configurations, however, are possible, particularly with the use of mirrors or other deflections devices as one skilled in the art would recognize. In any case, light sources 16 may include any suitable light sources known in the art, including but not limited to light emitting diodes (LEDs) and filters 18 may be bandpass filters or any other suitable spectral filters known in the art. In general, the light emitted by light sources 16 may include light in any part of the visible and invisible wavelength spectrums.

In some cases, light sources 16 (and additional light sources as required) may be configured to emit light having different wavelengths or different wavelength bands (e.g., one of the light sources may be configured to emit red light and the other light source may be configured to emit green light). In this manner, the system may use light sources 16, lenses 17 and filters 18 to sequentially illuminate the particles with different wavelengths or different wavelength bands of light. For example, red light may be used to excite classification dyes that may be internal to the particles, and green light may be used to excite reporter molecules coupled to the surface of the particles. Since the classification illumination is dark during reporter measurements (i.e., in the above example, red light is not directed to the particles while green light is directed to the particles), the analyte measurement sensitivity of the system will not be reduced due to crosstalk from out of band light.

Although assay analysis system 10 is shown in FIG. 1 having two light sources, it is to be understood that the system may include any suitable number of light sources. In some embodiments, six light sources may be positioned in a circumferential or hexagonal arrangement to direct light onto the imaging plane of analysis chamber 12. In particular, light sources 16 may be arranged such that each light source directs light to particles in analysis chamber 12 from a different direction. In this manner, the light sources may be configured to provide an illumination "ring". Furthermore, although assay analysis system 10 is shown in FIG. 1 having two lenses associated with each light source, it is to be understood that the system may include any suitable number of lenses for each light source. For example, in some embodiments, the system may include three refractive lenses for each light source to collect as much light from the light sources as possible and near-collimate it before presentation to a filter. Though a single normal refractive lens can be used, two or more lenses may be advantageous to increase the collection angle and provide a more efficient illumination system.

As set forth above, the photosensitive detection subsystem of assay analysis system 10 includes imaging lens 20, filter/s 22 and photosensitive detector 24. In general, imaging lens 140 is configured to image light scattered and/or fluoresced from particles disposed within the imaging region of analysis chamber 12 onto photosensitive detector 24 via filter/s 22. Imaging lens 140 may include any suitable refractive optical element known in the art and filter/s 22 may include optical bandpass filters or any other suitable spectral filter/s known in the art. Photosensitive detector 24 may be a CCD, CMOS, or Quantum Dot camera or any other suitable imaging device known in the art which is configured to generate images. Although assay analysis system 10 is shown in FIG. 1 having a single photosensitive detector, the system may include any suitable number of photosensitive detectors as well as any number of filters and lens to aid in the generation of images.

In some cases, assay analysis system 10 may include a device configured to alternate different filters into the optical path of light exiting imaging lens 20, such as a filter wheel assembly, for example. In such cases, each of the detection filters may be configured to transmit light of a different wavelength or a different wavelength band. As such, the wavelength or wavelength band at which an image of particles is acquired by photosensitive detector 24 may vary depending on the position of the filter wheel assembly, which corresponds to the filter in the optical path of light exiting imaging lens 20. In this manner, a plurality of images of the particles may be formed sequentially by, imaging the particles, altering the position of the filter wheel, and repeating the imaging and altering steps until images at each wavelength or waveband of interest have been acquired by photosensitive detector 144. The system shown in FIG. 1 may, therefore, be configured to generate a plurality or series of images representing the fluorescent emission of particles at several wavelengths of interest.

As set forth above and shown in FIG. 1, assay analysis system 10 may, in some embodiments, include processing unit 26 operatively coupled (as denoted by the dotted lines in FIG. 1) to different components of the system, such as but not limited to components of analysis chamber 12, the illumination subsystem and the photosensitive subsystem. In other cases, however, assay analysis system 10 may not include a processing unit, but rather processing unit 26 may be a separate entity from assay analysis system 10. In such embodiments, assay analysis system 10 may be configured for connection to a processing unit in any suitable manner known in the art (e.g., via transmission media or one or more electronic components such as analog-to-digital converters). In any case, processing unit 26 may take various forms, including a personal computer system, mainframe computer system, workstation, network appliance, Internet appliance, personal digital assistant (PDA), a digital signal processor (DSP), field programmable gate array (FPGA), or other similar device.

In general, processing unit 26 includes a processor and a storage medium having program instructions which are executable via the processor for performing a number of operations on assay analysis system 10. For example, in addition to having program instructions to perform the processes set forth in FIGS. 4-6, processing unit 26 may be configured to acquire (e.g., receive) image data from photosensitive detector 24 and further process and analyze these images to determine one or more characteristics of particles such as a classification of the particles and information about a reaction taken place on the surface of the particles. The one or more characteristics may be output by the processing unit in any suitable format such as a data array with an entry for fluorescent magnitude for each particle for each wavelength.

In general, the term "storage medium," as used herein, may refer to any electronic medium configured to hold one or more set of program instructions, such as but not limited to a read-only memory, a random access memory, a magnetic or optical disk, or magnetic tape. The term "program instructions" may generally refer to commands within a program which are configured to perform a particular function, such as analyzing particle quantity and distribution within an imaging region of an assay analysis system or evaluating the performance of a focusing routine performed on an assay analysis system as described in more detail below. Program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired. Program instructions implementing the processes described herein may be transmitted over on a carrier medium such as a wire, cable, or wireless transmission link.

As noted above, some embodiments of the methods described herein involve generating a frequency spectrum of an image via a discrete Fourier transform and analyzing the frequency spectrum to obtain information about the state of the assay analysis system used to create the image. Alternatively stated, some embodiments of the invention use frequency-domain techniques to characterize particle quantity and distribution within an imaging volume as well as image focus. Theoretically, a particle may be represented by any number of pixels, specifically any number between one pixel, if the camera resolution is below the particle's size, or an infinite number of pixels, if the camera resolution is infinite. Therefore, particle image topography looks like a cube at the low end (i.e., a single pixel) and, at the high end (i.e., an infinite number pixels) due to the point spread function effect inherent of an imaging lens, the particle image topography will resemble the shape of the particle with its edges smoothed out into the background (e.g., the image topography of a spherical particle will look like a Gaussian function at the high end). The concept of using frequency-domain techniques to characterize particle quantity and distribution within an imaging volume as well as image focus is described below in reference to a single pixel representing a particle and an infinite number of pixels representing a particle, but it is to be understood that the concept may be applied to any number of pixels representing a particle. It is further noted that the actual transform used (e.g., a fast Fourier transform (FFT) or a discrete cosine transform (DCT)) will be applied with integration limits beyond the physical edges of the particle. As described throughout the disclosure, the embodiments of the invention are not limited these "frequency domain" techniques. Rather, in some embodiments, the frequency content of an image may be analyzed in the spatial domain (e.g., convolving the image with a high-pass filter kernel to isolate the higher frequency components in the spatial domain).

A frequency domain representation of an image contains a superposition of the contributions of all particles in the image. For simplicity, an image frequency spectrum may be conceptualized with respect to a single particle such as set forth below. To mathematically conceptualize a frequency spectrum generated via a discrete Fourier transform, the topography of a single rectangular pixel representing a particle, or any cuboid, may be represented by the following 2-dimensional step function:

$$f(t, z) = \int_{-T/2}^{T/2} \int_{-Z/2}^{Z/2} A \, dt dz$$

In such a function, t and z are a coordinate system, T and Z are respectively the horizontal and vertical lengths of the rectangular pixel and A is the brightness value of the pixel. The Fourier Transform of the above equation is:

$$F(u, v) = \int_{-T/2}^{T/2} \int_{-Z/2}^{Z/2} A e^{-j2\pi(ut+vz)} dt dz$$

resulting in a frequency spectrum that is defined by the following 2-D sinc function:

$$|F(u, v)| = ATZ \left| \frac{\sin(\pi u T)}{(\pi u T)} \right| \left| \frac{\sin(\pi v Z)}{(\pi v Z)} \right|$$

The peaks of such a sine function correspond to harmonics or multiples of the fundamental spatial frequency and the peak to peak spacing in the frequency domain is dependent on the edge lengths of the cuboid in the spatial domain before transformation. It is noted that the frequency spectrum of |F(u,v)| will contract if the size of the pixel increases or if the number of pixels representing a particle increases. The frequency spectrum of any shaped particle is related to the frequency spectrum of a rectangle since any single radial slice through the particle results in a step function. For example, the projection of a spherical particle on a 2-D plane can be decomposed as an infinite number of radial slices that each define a rectangle and, thus, the resultant spectrum also consists of equally spaced peaks, or harmonics. These same concepts may be applied to a high resolution image of a particle (i.e., cases in which an infinite number of pixels represent a particle). For example, a high resolution image of a spherical particle will generally appear as a circle without distinct edges as it just gradually fades into the background (i.e., similar to a Gaussian function). Without distinct edges, the harmonic content will be minimal and the frequency spectrum of such an image will itself be very close to a Gaussian function. In the case of a perfect spatial Gaussian shape, the discrete Fourier transform is Gaussian, with the widths of the two Gaussians (spatial and spectral) being inversely related.

Most particles being imaged, spheres included, will classify somewhere between a square and a Gaussian. Because infinite resolution is not possible, their spectrums will most likely exhibit harmonics in the direction of the edges caused by the pixels themselves, in addition to the shape of the particle. The methods described herein, thus, may be applied to a number of different shaped molecules by monitoring the brightness of the lobes, or harmonics, of their spectrums. It is particularly noted that the methods described herein may be applied to particles of any shape and, thus, are not limited to applications of spherical particles. A graph of an exemplary frequency spectrum of a spherical particle is shown in FIG. 2 having a primary lobe 27 and a radial harmonic 28. A cross-sectional view or profile of the graph depicted in FIG. 2 is shown in FIG. 3. FIGS. 2 and 3 are used in conjunction with the descriptions of the methods outlined in FIGS. 4-6, specifically in reference to processes of analyzing a frequency spectrum of an image. Although the frequency spectrum depicted in FIGS. 2 and 3 includes a single radial harmonic 28, it is noted that the frequency spectrums considered for the methods described herein are not necessarily so limited. In particular, frequency spectrums having more than one harmonic may be considered for the methods described herein. It is noted that, just as with a spectrum of a square or a circle, primary lobe 27 will contract if the sphere's diameter increases.

In general, any type of particle may be used for the methods described herein. In some cases, particles serving as vehicles for molecular reactions may be particularly applicable for the methods described herein. Exemplary molecular reaction particles which are used in imaging systems include xMAP® microspheres, which may be obtained commercially from Luminex Corporation of Austin, Tex. The term "particle" is used herein to generally refer to microparticles, microspheres, polystyrene beads, quantum dots, nanodots, nanoparticles, nanoshells, beads, microbeads, latex particles, latex beads, fluorescent beads, fluorescent particles, colored particles, colored beads, tissue, cells, micro-organisms, organic matter, non-organic matter, or any other discrete substrates or substances known in the art. Any of such terms may be used interchangeably herein.

Turning to FIGS. 4A and B, method are provided for analyzing particle quantity and distribution within an imaging region of an optical assay analysis system as particles are loaded into the imaging region to determine when to terminate the loading of particles into the imaging region. As shown in block 30 of FIG. 4A, an embodiment of a method includes successively imaging an imaging region of an assay analysis system as particles are loaded into the imaging region. The frequency of imaging may be preset and may generally be any frequency deemed appropriate for the assay analysis system, particularly depending on the flow rate the fluid assay is introduced into the imaging region, the processing speed of the photosensitive detection subsystem of the assay analysis system, and the desired precision for identifying a point at which particles start to accumulate and/or cluster within the imaging region. An exemplary frequency of imaging may be between every 1 to 5 milliseconds. A frequency spectrum of each image is generated via a discrete Fourier transform as noted in block 32. The frequency spectrums are specifically generated upon formation of each image (i.e., immediately after the formation of each image) such that the routine outlined in FIG. 4A is performed in real-time (i.e., as particles are being loaded into the imaging region). The frequency spectrums may be generated via a fast Fourier transform (FFT) or a discrete cosine transform (DCT), both of which are categorized as discrete Fourier transforms. In general, FFTs are considered a more complete frequency analysis tool than DCTs, but DCTs are much faster to compute than FFTs. Thus, there is generally a trade-off of which transform to employ.

The method continues to block 34 in which the same coordinate portion of each frequency spectrum is integrated. The "same coordinate portion" generally refers to the same, two-dimensional or three-dimensional portion of each frequency spectrum as addressed by the spectrums' coordinates. The same coordinate portion may be any portion of the frequency spectrums, but for reasons set forth below, it may be advantageous for the same coordinate portion to be within a high frequency portion of each spectrum. As further noted below, it may be advantageous for the same coordinate portion to include a portion of a harmonic within each frequency spectrum. In general, each spectrum will get brighter as more particles populate the imaging volume. At some point during the transfer of particles into the imaging region, the particles will begin to crowd around and/or cluster with other particles and, as they do, the frequency spectrums will begin to be biased towards the lower frequencies since reflections off of many of the particle edges that contribute to the higher frequencies of the spectrum will be smoothed, reduced, or removed. In other words, the brightness gradient at the higher frequencies of the frequency spectrums will start to decrease and the brightness gradient at the lower frequencies of the frequency spectrums will increase at some point since a higher proportion of the brightness contributed to the spectrum by incoming particles will register in the lower frequencies.

Based on such changes to the frequency spectrums, a portion of the frequency spectrums may be monitored (i.e., by taking an integral of such a portion) to determine at which point to terminate the loading of particles within the imaging region, specifically to inhibit or minimize the crowding and/or clustering of particles within the imaging region. In other words, a portion of the frequency spectrums may be monitored to indicate when the imaging volume is "full" but not overcrowded. This technique is very powerful because it requires very little knowledge about the particles being loaded into the volume and it can identify the proper "load point" for an infinite number of distributions without adjustment. Since the accumulation and/or clustering of particles within the imaging region will facilitate a change to the brightness gradients in the higher frequency portion and the lower frequency portion of the spectrums, portions within either the higher frequency portion or the lower frequency portion may be monitored to terminate the loading of particles within the imaging region. In some cases, however, the lower frequency portions of the spectrums may contain increases in brightness caused by rising levels of background light and, thus, decreases of the brightness gradient in the lower frequency portions of a spectrum due to particle accumulation and/or clustering in the imaging region may be slight. Since the high frequency portions of the spectrum are not indicative of levels of background light in an image, it may be advantageous, in some cases, for the same coordinate portion integrated at block 34 to be within a high frequency portion of each spectrum.

In general, the primary lobe of a frequency spectrum represents the low frequency portion of light within an image and the portions of the spectrum extending out from the primary lobe, particularly the harmonics, represent the high frequency portion of light within an image. For example, in reference to FIGS. 2 and 3, primary lobe 27 represents the low frequency portion of the image and harmonic 28 represents the high frequency portion of the image. As such, in some embodiments, the same coordinate portion integrated at block 34 may include a portion of a harmonic within each frequency spectrum. In any case, in embodiments in which the high frequency portion of the spectrums are monitored for the integration process outlined in block 34, the same coordinate portion may include any portion of the spectrum outward from the primary lobe. For instance, the same coordinate portion may, in some embodiments, be the entire area of the spectrum outward from the primary lobe. In other cases, the same coordinate portion may be a line extending from the base of the primary lobe out to the corner of the spectrum. Other portions of the high frequency portion of the spectrum may also be considered for the integral computations.

In some cases, the same coordinate portion integrated at block 34 may be preset before the method outlined in FIG. 4A commences. In other embodiments, however, the method may include analyzing at least the first frequency spectrum generated in the routine to select a basis point from which to establish the same specified portion of each frequency spectrum to be integrated, as shown in block 40. Such a process may generally include analyzing at least the first frequency spectrum to determine the extent of the primary lobe and selecting the basis point based on thereon, such as at the base of the primary lobe (i.e., the low point between the primary lobe and the harmonic) or the basis point at a point offset and outward from the base of the primary lobe. An exemplary analysis routine may involve computing a moving average of brightness between a center of the spectrum and a corner point of the spectrum to determine the base of the primary lobe, specifically analyzing the moving average computations and assigning the base of the primary lobe when the moving average first starts to increase. Other manners of determining the base of the primary lobe, however, may be used.

In any case, the process of analyzing a frequency spectrum to select a basis point for establishing the portion of each frequency spectrum to be integrated may, in some embodiments, be done solely at the first generated frequency spectrum. In other cases, the process of analyzing a frequency spectrum to select a basis point for establishing the portion of each frequency spectrum to be integrated may be done at each frequency spectrum generated or, alternatively, may be done in a periodic manner relative to the generation of the frequency spectrums, such as but not limited to every other frequency spectrum which is generated. It is noted that the process of analyzing at least the first generated frequency spectrum to select a basis point for establishing the portion of each frequency spectrum to be integrated is optional and, thus, block 40 may be omitted from the method in some cases. Block 40 is outlined by a dotted line in FIG. 4A to indicate that it is an optional process.

Regardless of whether the same specified portion of the frequency spectrums integrated for block 34 is preset or established by analysis of at least one of the frequency spectrums, the method outlined in FIG. 4A includes terminating the loading of particle into the imaging region upon computing an integral which meets a criterion preset for the system. The termination of particle loading may include any manner known in the art, such as but not limited to closing a valve at any point in the fluid transmission lines feeding the imaging region or halting a pump feeding the fluid assay. In some embodiments, particle loading may be terminated upon computing an integral which crosses a predetermined threshold as noted in block 36. In general, the predetermined threshold may be a particular integral value, which may vary among applications and systems and may generally be set based on the brightness of the light to be reflected from the particles and the desired precision for identifying a point at which particles start to accumulate and/or cluster within the imaging chamber. In other cases, the loading of particles into the imaging region may be terminated upon detecting a change in integral magnitude less than a preset limit between frequency spectrums generated in succession as noted in block 44. In some embodiments, the process outlined in block 44 may include terminating the loading of particles upon detecting a change in the rate of increase of the successively computed integrals. In any case, as noted in block 42, the method outlined in FIG. 4A may generally include tracking the integrals calculated for the successively generated frequency spectrums prior to terminating particle loading based upon detecting a change in integral magnitude.

In some cases, the preset limit set forth in block 44 corresponding to the change in integral magnitude by which to terminate the loading of particles may be a particular value preassigned to the system or assay. In particular, the preset limit may be set prior to the processing of the assay. In such embodiments, the preset limit may include any threshold deemed applicable for the assay and/or system, depending on the brightness of the light to be reflected from the particles and the desired precision for identifying a point at which particles start to accumulate and/or cluster within the imaging chamber. In other cases, the preset limit set forth in block 44 by which to terminate the loading of particles may be based on changes in integral magnitude between two or more of the frequency spectrums as noted in block 46. In particular, such a process may involve measuring changes in integral magnitude between two frequency spectrums measured in succession and setting the preset limit to be the measured change or less than the measured change.

The process outlined in block 46 may be performed on the first two generated frequency spectrums and, in some cases, for each frequency spectrum generated thereafter. Alternatively, the process may be performed in a periodic manner relative to the generation of the frequency spectrums, but not on all of the frequency spectrums. It is noted that the process of setting the limit by which to terminate particle loading based on changes in integral magnitude is optional and, thus, block 46 may be omitted from the method in some cases. Block 46 is outlined by a dotted line in FIG. 4A to indicate that it is an optional process. An exemplary manner for conducting the processes denoted in blocks 42, 46, and 44 includes graphing the integral magnitudes for the process of block 42 and monitoring a slope of the graph for the process of block 46. The process of monitoring the slope of the graph may generally be used to set the preset limit by which to terminate particle loading and, thus, upon detecting a change in the slope, the loading of the particles may be terminated as set forth in block 44.

FIG. 4B denotes an alternative method for analyzing particle quantity and distribution within an imaging region of an optical assay analysis system as particles are loaded into the imaging region to determine when to terminate the loading of particles into the imaging region. As depicted in FIG. 4B, embodiments of the method presented proceed in a similar manner to FIG. 4B. Moreover, the method proceeds by analyzing the particle quantity and distribution within an imaging region of an optical assay analysis system by analyzing the frequency content of successive images as particles are loaded into the imaging reason. Moreover, based on the frequency content of these successive images, it may be determined when to terminate the loading of the particles. However, instead of performing the steps of generating the a frequency spectrum of each image and integrating a coordinate portion of each frequency spectrum, as indicated in blocks 32 and 34, the embodiments of the method denoted in FIG. 4B analyze the images differently. Rather than converting the images to the frequency domain, the analysis if the frequency content of the images is performed in the spatial domain.

Instead of generating a frequency spectrum and analyzing the higher frequency portions of that frequency spectrum as described with respect to specific embodiments of FIG. 4A, embodiments of the method in FIG. 4B proceed by generating a convolved spatial image by convolving each image with a convolution kernel as denoted in block 33. As discussed in detail above, when analyzing an image of the particles that may be used with some embodiments of the methods, the higher frequency components of the images may be found in the edges of the particles. In preferred embodiments, convolving each successive image with the convolution kernel may act as a filter designed to isolate various higher frequency components. In some embodiments, the convolution kernel may be configured to act as a high pass filter—filtering out the lower frequency components of the images and leaving the higher frequency components. In some embodiments, the convolution kernel may be configured to act a band pass filter—filtering out both lower and higher frequency components to focus on a specific frequency band.

To apply a filter to a frequency spectrum in the frequency domain, the spectrum may be multiplied by a filter function. As is well known in the art, multiplication by a function in the frequency domain is mathematically equivalent to convolution of the inverse fourier transform in the spatial domain. As such, in specific embodiments, the convolution kernel be created based on the inverse Fourier transform of the filter function that would be applied to the image spectrum to filter frequencies in the frequency domain. For example, the frequency components left in the image after convolving the image with the filter kernel may correspond to the same "portions of the frequency spectrums" discussed with regard to blocks 34 and 40 above (e.g., a portion of the frequency spectrum moving outward from the primary lobe). Specifically, as denoted in block 34 of FIG. 4A, the method proceeds, in some embodiments, by the "same coordinate portion" of each frequency spectrum, so that portion may be integrated. In some embodiments, filter kernel may be created based on the inverse Fourier transform of a filter function designed to keep frequency components in these coordinate portions. Effectively then, convolving the filter kernel with the image to produced the convolved spatial image will have the same effect as isolating certain frequencies in the frequency domain.

Thus, integrating at least a portion of the convolved spatial image as denoted in block 35 will provide information regarding the frequency content of the images. As described in detail above, based on such changes to the frequency content of the successive images (as calculated by the integral of the convolved spatial image), it may be determined at which point to terminate the loading of particles within the imaging region, or specifically to inhibit or minimize the crowding and/or clustering of particles within the imaging region.

The remaining blocks of the embodiments of the method in FIG. 4B proceed similarly to the embodiments described with respect to FIG. 4A. That is, the embodiments of blocks 31, 33, 43, 45, and 47 correlate directly to the descriptions of their respective blocks 30, 32, 42, 44, and 46 described in FIG. 4A. The specifics of the various blocks are not repeated for the sake of brevity.

FIG. 5 denotes a method for analyzing particle quantity and distribution within an imaging region of an optical assay analysis system to determine if enough particles are present in the imaging region for further processes by the assay analysis system. As shown in blocks 50 and 52 of FIG. 5, the method includes generating a frequency spectrum of an image via a discrete Fourier transform and integrating a portion of the frequency spectrum. As with the frequency spectrum generation step described in reference to FIG. 4A, the frequency spectrum for block 50 may be generated via a fast Fourier transform (FFT) or a discrete cosine transform (DCT). Further in reference to the description of FIG. 4A, the integration step in block 52 may be applied to any portion of the frequency spectrum, but it may be advantageous for the portion to be within a high frequency portion of the spectrum and to further include a portion of a harmonic within the frequency spectrum. The specifics with regard to the options for generating a frequency spectrum and integrating a portion of the spectrum described in reference to blocks 32 and 34 of FIG. 4A are referenced for blocks 50 and 52 of FIG. 5 and are not reiterated for the sake of brevity. Furthermore, as discussed with respect to FIG. 4B, the steps of generating a frequency spectrum of an image and integrating a portion of the frequency spectrum may be performed instead by generating a convolved spatial image and integrating at least a portion of the convolved spatial image.

As shown in FIG. 5, a determination is made at block 53 regarding whether the integral computed at block 52 is greater than a predetermined threshold. The predetermined threshold may be any threshold deemed applicable for the assay and/or system, depending on the brightness of the light to be reflected from the particles and the desired precision for determining whether a sufficient amount of particles are present in the imaging chamber for further processes of the assay analysis system. The further processes considered for the method outlined in FIG. 5 may generally include any process which is particle-dependent and, specifically, any process of which performance depends on having a certain quantity of particles present in the imaging region. Exemplary processes include but are not limited to analyzing particles within the imaging chamber for the detection and quantification of one or more analytes of interest within a sample and analyzing particles within the imaging chamber to perform an accurate autofocus routine. In any case, the method may include sending a signal indicating enough particles are in the imaging region for further processes by the assay analysis system upon calculating an integral greater than the predetermined threshold as shown in block 54. On the contrary, the method includes sending a different signal indicating not enough particles are in the imaging region for further processes by the assay analysis system upon calculating an integral less than the predetermined threshold as denoted in block 56.

In some cases, the process may terminate upon either signal being sent. In other cases, however, the method may continue after the signal referenced in block 56 is sent, specifically in an effort to increase the particle quantity in the imaging chamber for further processes of the assay analysis system. In particular, as denoted by block 58, the method may include loading additional particles into the imaging region upon the signal referenced in block 56 is sent. In addition, the method may include generating an additional image of the imaging region subsequent to loading the additional particles into the imaging region as denoted in block 59. As shown in FIG. 5, the method routes back to repeat the processes outlined in blocks 50, 52, 53, and 54 or 56. In some cases, the processes outlined in blocks 58, 59, 50, 52 and 53 may be reiterated until a signal is sent for block 54 or until a predetermined number of iterations is conducted. It is noted that the processes of loading additional particles into the imaging region and generating an additional image of the imaging region are optional and, thus, blocks 58 and 59 may be omitted from the method in some cases. Blocks 58 and 59 are outlined by dotted lines in FIG. 5 to indicate that they are optional processes.

FIG. 6 denotes a method for evaluating the performance of a focusing routine performed on an assay analysis system. As shown in block 60 of FIG. 6, the method includes performing an automated routine to optimize a focal position of a photosensitive detection subsystem of an assay analysis system. Such a routine may generally be specific to the assay analysis system and, may be even more specific to the photosensitive detection subsystem included in the assay analysis system and, thus, may vary widely. In any case, the method includes imaging particles arranged within an imaging region of the assay analysis system subsequent to performing the automated routine as denoted in block 62. Thereafter, a frequency spectrum of the image may be generated via a discrete Fourier transform as shown in block 64. As with the frequency spectrum generation step described in reference to FIG. 4, the frequency spectrum for block 64 may be generated via a fast Fourier transform (FFT) or a discrete cosine transform (DCT).

In either case, the method continues to block 66 to compare a width of a primary lobe of the frequency spectrum at a designated brightness value to a benchmark to evaluate the performance of the automated routine. In some cases, the benchmark may be derived experimentally apart from the assay analysis system. In other embodiments, the benchmark may be based on a historic record of primary lobe widths at the designated brightness value stored in the assay analysis system, specifically from frequency spectrums generated from images previously obtained by the assay analysis system. In particular, in some cases, primary lobe widths from different frequency spectrums may be stored within a database of the assay analysis system such that a historic record can be maintained. The recording of the primary lobe widths may be performed each time the method outlined in FIG. 6 is performed for an assay analysis system or may be performed in a periodic manner relative to the number of times the method is conducted. Further to such a concept, the method outlined in FIG. 6 (i.e., the processes referenced in blocks 60, 62, 64 and 66) may be repeated at a set frequency relative to the number of times the automated routine is performed for the assay analysis system. The set frequency may be any frequency deemed appropriate for the assay analysis system, particularly depending on the desired precision for evaluating the performance of a focusing routine.

It will be appreciated to those skilled in the art having the benefit of this disclosure that this invention is believed to provide methods, storage mediums, and systems for analyzing particle quantity and distribution within an imaging region of an assay analysis system. In addition, methods, storage mediums, and systems for evaluating the performance of a focusing routine performed on an assay analysis system are provided. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A non-transitory storage medium comprising program instructions which are executable by a processor for:
    successively imaging an imaging region of an assay analysis system as particles are loaded into the imaging region;
    generating a frequency spectrum of each image via a discrete Fourier transform upon formation of each image;
    for each generated frequency spectrum, calculating a frequency domain integral for a selected portion thereof, wherein the selected portion is the same for each integral; and
    terminating the loading of particles into the imaging region upon computing an integral which crosses a predetermined threshold.

2. The storage medium of claim 1, wherein the frequency spectrum for each image is generated via a fast Fourier transform.

3. The storage medium of claim 1, wherein the frequency spectrum for each image is generated via a discrete cosine transform.

4. The storage medium of claim 1, wherein the selected portion of each frequency spectrum is within a high frequency portion of each frequency spectrum.

5. The storage medium of claim 1, wherein the selected portion of each frequency spectrum comprises a portion of a harmonic within each frequency spectrum.

6. The storage medium of claim 1, further comprising program instructions executable by the processor for analyzing at least a first of the generated frequency spectrums to select a basis point from which to establish the selected portion of each frequency spectrum to be integrated.

7. A non-transitory storage medium comprising program instructions which are executable by a processor for:
    successively imaging an imaging region of an assay analysis system as particles are loaded into the imaging region;
    generating a frequency spectrum of each image via a discrete Fourier transform upon formation of each image;

for each generated frequency spectrum, calculating a frequency domain integral for a selected portion thereof, wherein the selected portion is the same for each integral;

tracking the integrals calculated for the successively generated frequency spectrums; and terminating the loading of particles upon detecting a change in integral magnitude less than a present limit between two frequency spectrums generated in succession.

8. The storage medium of claim 7, wherein the frequency spectrum for each image is generated via a fast Fourier transform.

9. The storage medium of claim 7, wherein the frequency spectrum for each image is generated via a discrete cosine transform.

10. The storage medium of claim 7, wherein the selected portion of each frequency spectrum is within a high frequency portion of each frequency spectrum.

11. The storage medium of claim 7, further comprising program instructions executable by the processor for setting the preset limit based on changes in integral magnitude between two or more of the frequency spectrums.

12. An assay analysis system, comprising:
an analysis chamber;
an illumination subsystem configured to illuminate an imaging region of the analysis chamber;
a photosensitive detection subsystem configured to image particles arranged within the imaging region of the analysis chamber when illuminated; and
a non-transitory computer readable medium with program instructions thereon which are executable by a processor for:
generating, via a discrete Fourier transform, a frequency spectrum of an image generated by the photosensitive detection subsystem;
integrating a portion of the frequency spectrum;
upon calculating an integral greater than a predetermined threshold, sending a first signal indicating that enough particles are in the imaging region for further processes by the assay analysis system; and
upon calculating an integral less than the predetermined threshold, sending a second signal indicating that not enough particles are in the imaging region for further processes by the assay analysis system.

13. The assay analysis system of claim 12, wherein the frequency spectrum is generated via a fast Fourier transform.

14. The assay analysis system of claim 12, wherein the frequency spectrum is generated via a discrete cosine transform.

15. The assay analysis system of claim 12, wherein the portion of the frequency spectrum is within a high frequency portion of the frequency spectrum.

16. The assay analysis system of claim 12, wherein the portion of the frequency spectrum comprises a portion of a harmonic within the frequency spectrum.

17. The assay analysis system of claim 12, wherein the program instructions are further executable by the processor for:
loading additional particles into the imaging region upon sending the second signal;
generating an additional image of the imaging region subsequent to loading the additional particles into the imaging region;
repeating the steps of generating a frequency spectrum, integrating a portion of the frequency spectrum, and sending a first signal or second signal for the additional image; and
reiterating the steps of loading additional particles into the imaging region, generating an additional image, generating a frequency spectrum, integrating a portion of the frequency spectrum, and sending a first signal or second signal for each additional image until a first signal is sent or until a predetermined number of iterations is conducted.

18. A non-transitory storage medium comprising program instructions which are executable by a processor for:
successively imaging an imaging region of an assay analysis system as particles are loaded into the imaging region;
generating a convolved spatial image of each image by convolving each image with a filter kernel;
integrating at least a portion of each convolved spatial image; and
terminating the loading of particles into the imaging region upon computing an integral which crosses a predetermined threshold.

19. An assay analysis system, comprising:
an analysis chamber;
an illumination subsystem configured to illuminate an imaging region of the analysis chamber;
a photosensitive detection subsystem configured to image particles arranged within the imaging region of the analysis chamber when illuminated; and
a non-transitory computer readable medium with program instructions thereon which are executable by a processor for:
generating a convolved spatial image of an image generated by the photosensitive detection subsystem;
integrating at least a portion of the convolved spatial image;
upon calculating an integral greater than a predetermined threshold, sending a first signal indicating that enough particles are in the imaging region for further processes by the assay analysis system; and
upon calculating an integral less than the predetermined threshold, sending a second signal indicating that not enough particles are in the imaging region for further processes by the assay analysis system.

20. The assay analysis system of claim 19, wherein the program instructions are further executable by the processor for:
loading additional particles into the imaging region upon sending the second signal;
generating an additional image of the imaging region subsequent to loading the additional particles into the imaging region;
repeating the steps of generating a convolved spatial image, integrating at least a portion of the convolved spatial image, and sending a first signal or second signal for the additional image; and
reiterating the steps of loading additional particles into the imaging region, generating an additional image, generating a convolved spatial image, integrating at least a portion of the convolved spatial image, and sending a first signal or second signal for each additional image until a first signal is sent or until a predetermined number of iterations is conducted.

* * * * *